United States Patent [19]

Long, Jr.

[11] Patent Number: 4,927,623

[45] Date of Patent: May 22, 1990

[54] DISSOLUTION OF GAS IN A FLUOROCARBON LIQUID

[75] Inventor: David M. Long, Jr., San Diego, Calif.

[73] Assignee: Alliance Pharmaceutical Corp., San Diego, Calif.

[21] Appl. No.: 140,543

[22] Filed: Jan. 4, 1988

Related U.S. Application Data

[63] Continuation-in-part of Ser. No. 818,690, Jan. 14, 1986, Pat. No. 4,865,836, which is a continuation-in-part of Ser. No. 82,846, Aug. 5, 1987.

[51] Int. Cl.$^5$ .................... A61K 49/04; A61K 47/00
[52] U.S. Cl. ........................................ 424/5; 514/772; 514/832
[58] Field of Search ............... 424/5; 514/772, 832

[56] References Cited

U.S. PATENT DOCUMENTS

| | | | |
|---|---|---|---|
| 3,818,229 | 6/1974 | Long, Jr. | 250/323 X |
| 3,975,512 | 8/1976 | Long | 424/5 |
| 4,073,879 | 3/1978 | Long, Jr. | 424/5 |
| 4,105,798 | 8/1978 | Moore et al. | 514/756 |
| 4,116,336 | 9/1978 | Sorensen et al. | 206/524.8 |
| 4,146,499 | 2/1979 | Rosano | 252/196 |
| 4,151,108 | 4/1979 | Sorensen et al. | 252/408 |
| 4,163,734 | 8/1979 | Sorensen et al. | 252/408 |
| 4,299,728 | 11/1981 | Cormier et al. | 252/408 |
| 4,369,127 | 1/1983 | Cormier et al. | 436/111 |
| 4,397,870 | 8/1983 | Sloviter | 424/350 |
| 4,423,077 | 12/1983 | Sloviter | 424/325 |
| 4,451,251 | 5/1984 | Osnterholm | 600/24 |
| 4,769,241 | 9/1988 | Heldebrant et al. | 514/832 |

FOREIGN PATENT DOCUMENTS

| | | |
|---|---|---|
| 0220153 | 10/1986 | European Pat. Off. . |
| 0231091 | 1/1987 | European Pat. Off. . |
| 580328 | 8/1981 | Japan . |
| 590462 | 9/1982 | Japan . |
| 590672 | 10/1982 | Japan . |
| 601666 | 2/1984 | Japan . |

OTHER PUBLICATIONS

Riess, J. G., Artificial Organs, 8:49, (1984).

Mottram, J. C., British Journal of Radiology, 8:32, (1983S).

(List continued on next page.)

*Primary Examiner*—Frederick E. Waddell
*Attorney, Agent, or Firm*—Knobbe, Martens, Olson & Bear

[57] ABSTRACT

Biocompatible fluorocarbon emulsions having fluorocarbon in concentrations of from 75% weight per volume to 125% weight per volume have small, biocompatible particle size stability through heat sterilization with one emulsifying agent, including phospholipids, in concentrations of from 3% to 7% weight per volume. The single emulsifying agent can be hydrogenated lecithins and synthesized lecithins. Fluorocarbon emulsions having fluorocarbon in concentrations of from 40% weight per volume to 125% weight per volume have stability of partial pressure of oxygen and of partial pressure of carbon dioxide through heat sterilization and storage for extended periods of time after having been oxygenated with dissolved oxygen. A method of preparing biocompatible fluorocarbon emulsions includes preparing a mixture of an emulsifying agent, osmotic agent, buffering agent, aqueous phase and fluorocarbon, forcing the mixture under high pressure into a cavity, against a surface and around a lip to cause turbulence and possibly cavitation to form high fluorocarbon concentration emulsions that are stable through heat sterilization; and, even when oxygenated, maintain substantially stable partial pressures of oxygen and of carbon dioxide, and substantially stable pH. A method of oxygenating high fluorocarbon concentration emulsions includes placing a measured amount of the emulsion in a container and causing the emulsion to form a thin film around the inner surface of the container when the oxygen is injected. An alternative method of oxygenating the high fluorocarbon concentration emulsion includes a two container system where one container, permeable to the to be dissolved gas, is formed within the other, and the emulsion is injected in one container and the to be dissolved gas is injected into the other container.

11 Claims, 3 Drawing Sheets

OTHER PUBLICATIONS

Davis, S. S., Advances in Clinical Nutrition MTP Press, Ltd., Boston: 1982, pp. 228–229.

Goodin et al., 245 American Journal of Physiology, pp. H519–H523, (1983).

Geyer, R., Perfluorocarbon Blood Substitutes, Intl. Symp. on Artificial Blood Substitutes, Bari, Italy: Jun. 19–20, (1987), pp. 45–47.

Persico, D., et al., Journal of Org. Chem., 50:5156–5159, (1985).

Sharts, C. and H. Reese, J. Fluorine Chemistry, 11:637–641, (1978).

Yokoyama, K. et al., Fed. Proc., 34(6), 1478–1483, (1975).

Steiner, M. and J. Anastasi, J. Clin. Inv., 57:732–737, (1976).

Pandolfe, W. D. and R. R. Kinney, The National Meeting of the Amer. Inst. of Chem. Engin., Denver, Colo., Aug. 29, 1983.

Gould, S. et al., Assessment of a 35% Flurorcarbon Emulsion, J. of Trauma, 23(8):720–724, (1983).

Moss, G. Biomaterials, Artificial Cells, Artificial Organs, 15(2):333–336, (1987).

Geyer, R., Perfluorocarbons as Oxygen Transport Vehicles, 15(2):329–332, (1987).

Burgan, A., D. M. Long et al., 3rd Intl. Symp. on Blood Substitutes, Montreal: Jun. 18–22, (1987).

Police, A. M. et al., Critical Care Medicine, 12(2):96–98, (1985).

Bose, B. et al., Brain Research, 328:223–231, (1985).

Spears, J. et al., Circulation, (Abstracts), 68, (Supp. III), No. 317, Oct. 1983.

Ogbilby, J. et al., (with C. Long), American Heart Association, Nov. 16–19, 1987.

Nunn, G. R. et al., American J. of Cardiology, 52:203–205, (1983).

Patel, M. et al., Federation Proceedings, 29(5):1740–1745, (1970).

Itoh, Y. et al., Gan To Kagaku Ryoho, 11(4):864–72, (1984).

Rockwell, S., 3rd Intl. Symp. on Blood Substitutes, Montreal: Jun. 18–22, 1987.

Peck, W. W. et al., Invest. Radiology, 19:129, (1984).

Dobben, G. et al., Neuroadiology, 6:17–19, (1973).

Brahme, F. et al., Perfluorocarbon Bromides as Contast Media in Radiography of the Central Nervous System, Acta Radiologica, Supplemen, 347:459–466, (1975).

Liu, M. S. et al., "Myelography with Ferfluoroctylbromide: Comparison with Pantopaque", Investigative Radiology, 11(4):319–330, (1976).

Mattrey, R. F., Perfluorochemicals as U.S. Contrast Agents for Tumor Imaging and Hepatosplenography, Radiology, 163:339–343, (1987).

Mattrey, R. F., et al., 35th Annual Meeting of the Association of University Radiologists, Charleston, S.C., Mar. 22–27, (1987).

Long, D. M. et al., "Efficacy and Toxicity Studies with Radiopaque Perfluorocarbon," Radiology, 105(2):323–332, (1972).

Long, D. M. et al., Biomaterials, Artificial Cells, Artificial Organs, 15(2):417, Montreal: Jun. 18–22, (1987).

Arlen C., Long, D. M. et al., Biomaterials, Artificial Cells, Artificial Organs, vol. 15(2), pp. 431, Montreal: Jun. 18–22, (1987).

Burgan, A. et al., "Acute and Subacute Toxicity of 100% PFOB Emulsion", 5th Annual Mtng., Soc. of Magnetic Resonance in Medicine, Montreal: Aug. 18–22, (1986).

Long, D. et al., Intl. Symp., "Total Exchange Perfusion of Rats with Highly Concentrated Fluorocarbon Emulsions", Centenary of the Discovery of Fluorine, Paris: Aug. 25–29, (1986).

DISSOLUTION OF GAS IN A FLUOROCARBON LIQUID

RELATION TO RELATED APPLICATIONS

This application is a continuation-in-part of application Ser. No. 818,690 filed Jan. 14, 1986, now U.S. Pat. NO. 4,865,836, in the name of David M. Long, Jr. and entitled, "Brominated Perfluorocarbon Emulsions for Internal Animal Use for Contrast Enhancement and Oxygen Transport," and a continuation-in-part of application Ser. No. 82,846 filed Aug. 5, 1987 in the name of David M. Long, Jr. and entitled, "Biocompatible, Stable and Concentrated Fluorocarbon Emulsions for Contrast Enhancement and Oxygen Transport in Internal Animal Use." Priority of subject matter in this application common with subject matter in application Ser. Nos. 818,690 and Ser. No. 82,846 is hereby claimed.

BACKGROUND OF THE INVENTION

1. Field of the Invention:

The present invention relates to the art of biocompatible oxygen transport and contrast enhancement agents for animal use, and more particularly to biocompatibly fluid fluorocarbon containing emulsions having high fluorocarbon concentrations and substantial stability.

2. Description of the Prior Art:

In the past, fluorocarbons in aqueous emulsions with an emulsifying agent have been known for medical applications involving animals, including humans, for radiopacity and oxygen delivery. Oxygen and gases in general are highly soluble in some fluorocarbons. For example, see Long, U.S. letters Pat. No. 3,818,229; No. 3,975,512; and No. 4,073,879.

Efforts to use emulsified fluorocarbons as an oxygen carrier, as in a blood substitute, have encountered certain difficulties. Purity, non-toxicity, chemical and biological inertness and excretability of the ingredients, especially the fluorocarbons and any fluorocarbon emulsifying agents, as well as a high fluorocarbon concentration in the emulsion are desired objectives. The emulsion must be capable of sterilization, preferably by heat, have long-term particle size and function stability in the fluid or non-frozen state, preferably at ambient or room temperatures, be industrially feasible or capable of manufacture on a large scale, persist for sufficiently long times in the body blood stream when use intravascularly, be eliminated rapidly from the body thereafter and have a high enough concentration of the fluorocarbon while remaining biocompatibly fluid to be effective, whether as a contrast enhancement agent or as an oxygen carrier.

For intravenous and vascular uses, it is considered important to have small particle size. However, long term storage for extended periods of time for a month or longer, of fluorocarbon containing emulsions acceptable for intravascular use, i.e. with fluorocarbons having half retention times in the organs of approximately seven days or less such as is desirable for blood substitutes or "synthetic blood", has heretofore resulted in coalescence or conglomeration of the fluorocarbon particles in the emulsion into larger particles, especially during and after heat sterilization. For a general discussion of the objectives and a review of the efforts and problems in achieving these objectives in fluorocarbon blood substitutes, see "Reassessment of Criteria for the Selection of Perfluorochemicals for Second- Generation Blood Substitutes: Analysis of Structure/Property Relationship" by Jean G. Riess, 8 *Artificial Organs,* 34–56 (1984).

Particle sizes significantly larger than 0.4 micrometers (microns) tend to occlude small vessels and to collect too rapidly in the liver, spleen and some other organs, enlarging them and endangering their functioning. On the other hand, it is desired in certain applications to have sufficient emulsion particle size in order that the particles will collect around and in tumors, abscesses and infarcted myocardial tissue and infarctions in other tissues, and in the liver, spleen and bone marrow when fluorocarbons are used as a contrast enhancement medium. Larger particle sizes are unobjectionable when used in other, non-venous systems in the body, such as, for example, the trachea, the cerebrospinal fluid ventricles and other cavities of the body.

Herein in this specification, the term "weight per volume," "% weight per volume", "w/v" or "% w/v" will be used and should be understood to mean that ratio which is the weight in grams per 100 cubic centimeters or 100 milliliters, or equivalent expressions or mathematical identities thereof. This definition is meant to be consistent with that used in the field and which is given in, for example, the herein referenced patent to Sloviter. Thus, for example, an emulsion having a "5% w/v" of an ingredient has 5 grams of that ingredient per 100 ml of the final emulsion.

In the past, fluorocarbon emulsions particularly formulated for oxygen carriage have been taught to have upper limits on the fluorocarbon concentration. For example, efforts directed toward perfluorocarbon emulsions with phospholipid emulsifiers have been proposed having 20% to 40% weight per volume of the fluorocarbon and 2% to 6% weight per volume of lecithin, but such emulsions have a limited stability. Moreover, it has been taught that emulsions having fluorocarbon concentrations higher than 75% weight per volume are too viscous to be used intravascularly. See, for example, Sloviter, U.S. letters Pat. No. 4,423,077. Such concentrations, however, necessarily limit the capacity of the emulsion and the quantity of oxygen and of contrast enhancement which the emulsion can provide.

Moreover, the methods taught for achieving emulsions having higher fluorocarbon concentrations, on the order of from 50% to 75% weight per volume, required sonication for the turbulence or homogenization, and emulsification steps. Such methods, however, significantly limit the manufacturing or fabricating capability, for the quantities capable of fabrication using sonication are severely limited, and not considered of an industrial or commercial scale.

Moreover, it has been considered that higher weight per volume fluorocarbon concentrations were more toxic, apparently because it is more and too viscous. See, for example, Riess, cited above, 8 *Artificial Organs* (1984), at 49 where a 38% increase in mortality (50% versus 20%) is reported with the more concentrated 35% w/v fluorocarbon in emulsion than with the 20% w/v fluorocarbon in emulsion.

However, for many applications, such as percutaneous transluminal coronary angioplasty (PTCA), cerebral ischemia, organ preservation, myocardial infarction, as an adjunct to cancer radiation and chemotherapy and the like, higher fluorocarbon concentrations are desired for their higher oxygen dissolving capacity. The higher the concentration of the fluorocarbon, the less quantity of the emulsion that is needed to achieve the requisite contrast enhancement or quantity of oxygen to be administered. It is a medical desire and objective to minimize the total volume of medicines administered or inserted in a body. Further, it is desired to have higher concentration of oxygen to decrease the effects of hypoxia during ionic radiation treatments as described, for example, in J. C. Mottram, 8 *British Journal of Radiology*, at 32 (1935).

In other fluorocarbon emulsions, sterilization can only take place without damage to the emulsion, at temperatures lower than 121 degrees Centigrade (C.), on the order of, for example, 60 degrees C., and with repeated heatings. Many of these emulsions, further, must be stored frozen and thawed shortly before use, thus restricting handling and uses. Indeed, even in those emulsions previously taught as being sterilized at normal sterilizing temperatures, the desired emulsion is not obtained until centrifuging at 4 degrees C. at 100 times gravity for some period of time. See Sloviter, U.S. letters Pat. No. 4,423,077, mentioned above.

It should be noted, moreover, that the fluorocarbon F-decalin alone has heretofore been believed inconsistent or unstable in emulsion. This observation was made at fluorocarbon concentrations of 20% w/v, and it has been considered essential in order to achieve stability to add another fluorocarbon, such as F-tripropylamine, as in Fluosol-DC, a trade name for a blend of fluorocarbons in emulsion. It is believed that such a combination of fluorocarbons, however, merely cumulates the disadvantages of the individual fluorocarbon components in the resultant emulsion, and is generally undesirable. For example, notwithstanding the Fluosol-DA combination, the F-tripropylamine continues to have long retention times in the body. Moreover, Fluosol-DA must be stored in substantially the frozen state. Another effort to solve the problem of stability in using F-decalin was to increase the lecithin concentration to at least 7% weight per volume, and as high as 9% w/v. See Sloviter, mentioned hereinabove.

It has generally been thought that to increase fluorocarbon concentration in an emulsion, the concentration of the emulsifying agent must also be increased. Thus, the weight per volume of lecithin, when used as the emulsifying agent, must be increased in order to increase the concentration of fluorocarbon in the emulsion. See Sloviter, mentioned above, who describes a ratio of fluorocarbon to emulsifying agent in the emulsion of at most 10.7:1 by weight per volume, i.e. the emulsifying agent concentration is approximately 9.2% of that of the fluorocarbon concentration in emulsion.

Where yolk lecithin, a frequently chosen emulsifying agent because of its known biocompatibility, is used, the emulsion is subject to degradation in the presence of oxygen. Oxygen attacks normally available lecithin, such as yolk lecithin, to oxidize the lecithin molecule which may result in a possible introduction of toxicity and degradation of the emulsion. Thus, in the presence of oxygen, the pH of the emulsion decreases due to the accumulation of carbon dioxide and fatty acids, and the $pO_2$ pressure of the emulsion decreases. For this reason, it has been generally considered important to store such emulsions under or sparged with nitrogen which is believed to be inert with respect to the emulsion.

Yolk lecithin, as well as other lecithins have fatty acids characterized by one or more carbon-carbon double bonds. These double bonds are vulnerable to oxidation, leading to production of free fatty acids and other products. The lecithin thus changes into toxic components including fatty acids and lysolecithin which may produce adverse effects or toxicity. Over time, the oxygen dissolved in the fluorocarbon particle provides such an attack. To avoid such an attack, many such fluids are sparged with nitrogen and kept substantially oxygen free until use. A Pluronic, such as Pluronic F-68 is an emulsifying agent normally less sensitive to oxidation, but may cause undesirable reactions in some intravascular applications.

Oxygenation of the emulsion when used intravascularly in the body naturally occurs through the lungs. For many applications, however, such as percutaneous transluminal coronary angioplasty (PTCA), stroke therapy and organ preservation, it is highly desirable that the emulsion contain adequate oxygen prior to use or application. Not only when used as an oxygen carrier, but also in contrast enhancement applications where oxygen delivery to the contrasted body part also is desired, such as, for an example, in PTCA and stroke therapy through the cerebrospinal space, fluorocarbon emulsions are oxygenated in order to increase the amount of oxygen carried and delivered. The higher that the concentration of oxygen being carried in the emulsion is, the less of the emulsion that will be necessary to achieve the desired oxygen related objectives. Since excess volume alone may present biocompatibility problems, limitation of volume injected by attaining high fluorocarbon concentration in the emulsion is a desired objective.

When used for oxygen carriage or transport, fluorocarbon emulsions which cannot maintain substantially consistent partial oxygen pressure ($pO_2$) through sterilization, storage, processing and administration must be oxygenated immediately prior to use.

Frequently, however, it is desired to use fully oxygenated fluorocarbon emulsions at locations where oxygenation cannot be performed or is inconvenient, such as, for example, when treating myocardial tissue and other diseased tissue, when used as an adjunct with percutaneous transluminal coronary angioplasty, or when applying the emulsion at remote locations or in ambulances or field hospitals. Moreover, it is believed that some oxygenators de-stablize emulsions or catalyze emulsion breakdown. See, for example, Moore, et al., U.S. letters Pat. No. 4,105,798.

It is desired to provide a more uniform and more reliable pre-oxygenated, hence more immediately efficacious emulsion by performing the oxygenation during or shortly after the emulsion preparation before extended storage. Partial oxygen pressure ($pO_2$) and pH maintenance and stability during and through heat sterilization, and through extended time storage, preferably at room or ambient temperatures tend to indicate that there is no oxidation or degradation of the emulsion. It is a desired objective, therefore, to provide a biocompatible fluorocarbon emulsion which maintains $pO_2$ and pH during sterilization procedures and during extended periods of storage.

It is desired also to provide methods of oxygenating biocompatible fluorocarbons during or shortly after manufacture or fabrication.

It is desired further to provide fluorocarbon emulsions having a higher concentration of fluorocarbon in emulsion. It is desired yet further to provide such high fluorocarbon concentrations in emulsion with less concentrations of emulsifying agents, yet having biocompatibly satisfactory fluidity, i.e. biocompatibly low viscosity.

It is additionally desired to have methods of preparing and formulating high fluorocarbon concentrations with relatively low emulsifying agent concentrations in emulsion which do not have physical or practical commercial limitations affecting the quantity manufactured.

SUMMARY

In brief, in accordance with one aspect of the invention, biocompatibly fluid fluorocarbon emulsions having high concentrations of fluorocarbon are described which have heretofore been difficult or impossible to obtain. In addition, these emulsions have relatively less but effective amounts of emulsifying agents. The fluorocarbon emulsions are biocompatible for animal body uses, including intravascular use. The emulsions can be made by methods that provide large, commercially useable quantities, including mechanical mixing, such as relatively high pressure homogenization.

Some of these fluorocarbon emulsions may be oxygenated during or shortly after preparation and, even so, can be sterilized by conventional autoclave heat sterilization methods and remain stable, both in particle size and in partial pressure of oxygen, and through ambient or room temperature storage during accelerated shelf life studies and for extended periods of time, on the order of months. In another aspect of the present invention, some fluorocarbon emulsions, notably emulsions of 1-bromoheptadecafluoroctane ("PFOB") have been found to maintain consistency and stability through sterilization by gamma radiation.

Methods of oxygenation are described wherein the fluid fluorocarbon is placed in a container where the fluid forms essentially a layer on the inside wall of the container. Oxygen is placed inside the container and oxygenates the fluorocarbon. In other aspects of the invention, a flexible container is positioned within an outside container, which may or may not be flexible. The fluid fluorocarbon is placed within, alternatively, the inside container or the between the inside container and the outside container. The wall of the inside container comprises a gas permeable membrane so that oxygen placed in the inside container, or placed between the inside and the outside containers can permeate through the membrane to oxygenate the fluorocarbon placed in the other container.

A method of manufacturing or fabricating the emulsion comprises the preparation of a vehicle containing an emulsifying agent, osmotic agents and buffers. A fluorocarbon is blended into the vehicle, and the resulting mixture is forced at high pressure through a homogenizing path. The fluid mixture is forced against a surface and generally around some edge, creating a cavitation or similar turbulence. The fluid is recombined and withdrawn from the cavity in which the cavitation or similar turbulence takes place. Alternative methods include a division of the flow paths of the mixture and a re-directing of the flows at high speed or high pressure into each other, against a surface and withdrawal from the cavity in which the turbulence takes place.

DESCRIPTION OF THE PREFERRED EMBODIMENTS

A fluorocarbon emulsion comprises from 20% weight per volume to at least 125% weight per volume of a fluorocarbon or a highly fluorinated compound (hereafter called a "fluorocarbon". The fluorocarbon could be any fluorocarbon or fluorocarbon mixture which, in emulsion, is biocompatible. Such a fluorocarbon in the emulsion may be bis(F-alkyl)ethanes such as $C_4F_9CH=CHC_4F_9$ (sometimes designated "F-44E"), i—$C_3F_7CH=CHC_6F_{13}$ ("F-i36E"), and $C_6F_{13}CH=CHC_6F_{13}$ ("F-66E"); cyclic fluorocarbons, such as $C_{10}F_{18}$ ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tributylamine ("FTBA"), F-4-methyloctahydroquinolizine ("FMOQ"), F-n-methyldecahydroisoquinoline ("FMIQ"), F-n-methyldecahydroquinoline ("FHQ"), F-n-cyclohexylpyrrolidine ("FCHP") and F-2-butyltetrahydrofuran ("FC-75" or "RM101"). Other stable fluorocarbons in emulsion are monobrominated perfluorocarbons, such as 1-bromoheptadecafluoroctane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Additional stable fluorocarbon emulsions that can achieve small particle sizes and long shelf lives when made in accordance with this invention include perfluoroalkylated ethers or polyethers, such as $(CF_3)_2CFO(CF_2CF_2)_2OCF(CF_3)_2$, $(CF_3)_2CFO(CF_2CF_2)_3OCF(CF_3)$, $(CF_3)_2CFO(CF_2CF_2)_2F$, $(CF_3)_2CFO(CF_2CF_2)_3F$, $(C_6F_{13})_2O$ and $F[CF(CF)CF\ O]CHFCF$. Further, fluorocarbon-hydrocarbon compounds, such as, for example, $C_8F_{17}C_2H_5$ and $C_6F_{13}CH=CHC_6H_{13}$ can also be used in practicing the methods and achieving the emulsions of this invention.

Some fluorocarbons have vapor pressures too high for intravascular use. 1-bromotridecafluorohexane ($C_6F_{13}Br$) and F-2-butyltetrahydrofuran ("FC-75" or "RM-101") are two such fluorocarbons. Such fluorocarbons and their biocompatible emulsions may be used, however, in the respiratory system, gastrointestinal tract and cerebrospinal space, cavities and ventricles.

The fluorocarbon emulsion includes an emulsifying agent which must not reduce fluidity unnecessarily, and which will not permit viscosity to become so high that the emulsion will not be useful in the animal body. It has been discovered that very high fluorocarbon concentrations in emulsion, much higher than 76% weight per volume, can be achieved, including even on the order of 90%, 100% and 125% weights per volume but yet the viscosity of such emulsions remains suitable for use in the most constricted or limited body tissue, such as the vascular system, including the veins, arteries and lymphatics, and the cerebrospinal space.

In addition, these emulsions have been achieved with surprisingly low amounts of emulsifying agents. For example, with lecithin, which is an emulsifying agent of choice frequently used because of its known biocompatibility. Also, lecithin is used in fat emulsions for parenteral nutrition. Yet lecithin contributes to the increase in viscosity and is subject to attack by oxygen, the carriage of which is one of the major possible objects of fluorocarbon emulsions. It is believed that there is a relationship between the amount of lecithin and the viscosity, and that the lecithin per given weight contributes disproportionately more than do comparable weights of fluorocarbons towards increasing viscosity in emulsions.

Fluorocarbon emulsions having fluorocarbon concentrations of 90%, 100% and 125% weights per volume have been obtained which have small particle size stability through heat sterilization and through storage for extended periods of time, on the order of months, at room or ambient temperatures using concentrations of lecithin in the emulsion of only 6%, 4.5% and 3.5% weights per volume where the mean particle sizes are in the range of approximately 100 nanometers (nm) to 300 nm in diameter. For emulsions having larger particle size means, even less lecithin is needed. For example, a 125% w/v of fluorocarbon in emulsion having a mean particle size of 600 nm has remained very stable through heat sterilization and through accelerated shelf life tests with only 3% w/v of lecithin. Such emulsion have a ratio of the fluorocarbon in emulsion to the emulsifying agent in emulsion of from 10:1, an emulsifying agent concentration which is approximately 10% of that of the fluorocarbon in emulsion, to 15:1, i.e., an emulsifying agent concentration which is approximately 6.7% of that of the fluorocarbon in emulsion, to as high as 41.7:1, i.e., an emulsifying agent concentration which is approximately 2.4% of that of the fluorocarbon in emulsion. These emulsions have been obtained by special mixing or homogenization procedures which do not require sonication and which can be formulated and manufactured more easily in large quantity.

Surprisingly, these emulsions are still very fluid, that is to say, they have a sufficiently low viscosity that is still compatible with vascular use, where the particle sizes are appropriate, and are otherwise suitable for other applications where relatively low viscosity is required.

The particles began to become larger, as shown by larger mean particle size measurements, at lecithin concentrations of around 3.5% weight per volume or less, where fluorocarbon concentrations are around 100% weight per volume. Such larger particle sizes could be useful for use in certain applications in animal body parts where larger particle sizes, such as, for example, 600 nm mean diameter, could be tolerated or even preferred.

Fluorocarbon emulsions having relatively high concentrations, on the order of 80% w/v to 125% w/v and having a relatively higher concentration of the emulsifying agent, on the order of 7% w/v to 14% w/v have a higher viscosity than the emulsions mentioned hereinabove. Some of these higher emulsifying agent concentration emulsions have a viscosity, when stirred or mixed, sufficient for holding to the skin in topical applications where the emulsion is exposed to the air. If a high amount of oxygen is dissolved into such an emulsion, the emulsion would be a good emollient. In burns, such a malagma could suitably coat the burn area to protect the skin from dirt, drying and bacterial contamination, yet the malagma would permit diffusion of oxygen to the burned skin. Such a high fluorocarbon concentration emulsion could have mixed therein additional ingredients, such as antibiotics, nutrients, steroids, corticosteroids and other medicines which may be gainfully employed in the treatment of burns. It is an advantage of the present invention that such high fluorocarbon concentration emulsions favorably have a high oxygen concentration and diffusiveness so that by permeability, the oxygen is delivered to the burned topical areas, while providing a protective barrier against microorganisms and dehydration.

Moreover, as described in greater detail herein, these emulsions, if they employ a lecithin emulsifying agent that is fully saturated with hydrogen and they are kept in a sealed container, they will maintain in solution the oxygen in the emulsion at ambient temperatures for substantial periods of time, making such an emollient expedient and highly useful for use by ordinary persons not necessarily trained in the medical arts.

It also has been discovered that some very highly concentrated fluorocarbon emulsions can be heavily oxygenated during and shortly after preparation of the emulsion, and remain heavily oxygenated during sterilization and through storage for extended periods of time when using an oxygen resistant surfactant as the emulsifying agent. Such a surfactant can be a lecithin which has been fully or substantially hydrogenated, that is to say where the double bonds have been saturated with hydrogen so as to make the lecithin resistent to oxygen attack. It has also been discovered that certain synthetic lecithins or lecithin analogs are resistant to oxidation, and in which the presence of sites sensitive to oxidation have been avoided. In a further possible emulsion, fluorinated surfactants which are resistant to oxidation can be made.

One of the advantages of using fluorocarbon emulsions is that the fluorocarbon, neat as well as in emulsion, absorbs and carries oxygen in significant amounts. Such oxygen, when carried in an emulsion compatible with blood, can be freed in the vascular capillaries to provide oxygen to the muscle and other tissue cells within the body. In such a use, the fluorocarbon emulsion becomes an oxygen and carbon dioxide transport, or "blood substitute," at least insofar as oxygen and carbon dioxide ($CO_2$) transport is concerned.

Oxygen, however, has significant additional advantages when carried in fluorocarbon emulsions. For example, it has been found that oxygen significantly potentiates the action of radiation and chemotherapy on cancer cells. It has been found that a fluorocarbon emulsion will transport oxygen around and into hypoxic cells of a tumor which would otherwise have at times less or no oxygen from the tumor's normal blood supply. Indeed, parts of tumors have a blood supply that is inadequate or is inadequate at times. The fluorocarbon in emulsion delivers oxygen around the tumor or around the parts of the tumor having an inadequate blood supply, and the oxygen diffuses through tissue and into such blood deprived areas of the tumor cells, as demonstrated by the reduction in the fraction of hypoxic cells in tumors treated with fluorocarbon emulsions. Oxygen then assists and potentiates the radiation and/or chemotherapy treatments directed toward such an oxygenated tumor.

Such highly oxygenated emulsions are also useful in the treatment of stroke victims, where oxygen transport to oxygen deprived brain tissue is exigent. The fluorocarbon emulsion could be distributed, for example, through the vascular system, as well as through the cerebral spinal cavities and ventricles.

Another use for highly oxygenated fluorocarbon emulsion is in percutaneous transluminal coronary angiography ("PTCA"), where it is important to pass oxygen through the induced blockage in order to provide oxygen to the vascular tissue system downstream from the blockage area. PTCA is a system in which a catheter is introduced carrying a balloon in an artery at a site where there is an atheromatous plaque, to compress the plaque and thereby enlarge and open the lumen. A lumen capillary within the catheter can be used to direct fluid through the fiber and through the inflatable balloon. Blood, however, is fragile and would likely be functionally damaged if forced through such a small capillary. Fluorocarbon emulsions, on the other hand, are known to be resistant to mechanical stresses, i.e. are not so fragile, but on the contrary are stable through substantial mechanical trauma including forced passage through such small lumens.

Another use for highly concentrated fluorocarbon, high oxygen carrying emulsions is in organ preservation. Transport of vital organs which require constant oxygen supply, from one location to another, for example, would be greatly facilitated by perfusion of the organ with an oxygenated fluorocarbon emulsion having the high concentrations and high fluidity of the present invention, as well as by immersing the organ in such an oxygenated emulsion that is stable and is biocompatible with the organ.

Another use of the high concentration fluorocarbon emulsion of the present invention is in enhancing the images formed by ultrasound techniques, particularly those obtained when using Doppler-effect techniques. Heretofore, it has been considered that the particle sizes of fluorocarbon emulsions suitable for vascular use would be too small for effective use of Doppler-effect ultrasound imaging techniques which are based on the reflection of sonic radiation off of or from moving objects such as blood cells. As will be seen from Example XXI below, good and even better images can be obtained when using Doppler-effect ultrasound techniques by employing the fluorocarbon emulsions of the present invention to enhance the contrast of circulating blood. Doppler-effect ultrasound imaging is used to form images of the blood vessels in which red blood cells flow.

Red blood cells reflect sonic radiation well. Sonic radiation, or sound waves transmitted in the direction of the blood vessels strike the red blood cells and are reflected back, or produce an echo. The reflected sonic radiation has a shift in pitch from the transmitted radiation, either higher or lower depending on the relative direction and velocity of the blood cell flow. Normally without the aid of any enhancement medium, the change or shift in frequency is detected only if the flow velocity is greater than 6 centimeters per second (cm/sec.).

It has been found the reflectivity of the sonic radiation from blood vessels is greatly increased when concentrated fluorocarbon emulsions of the present invention are given intravenously. The increased reflectivity improves the image quality when imaging arteries where flow velocity is normally high, as well as when imaging veins where velocity is relatively more slow. The improved image quality obtained when using the concentrated fluorocarbon emulsions of the present invention allows imaging of the fluorocarbon emulsion particles adjacent the walls of the veins where clot formation is initiated.

High fluorocarbon concentration emulsions may also be used in order to minimize storage and shipping space, and employed with the intention of diluting the fluorocarbon concentration prior to actual use in or with the body. Dilution can be accomplished simply by increasing the aqueous phase.

Fluorocarbon emulsions having a high concentration of the oxygen carrying fluorocarbon, but which are stable through heat sterilization and time storage at ambient or room temperatures, are particularly suitable and advantageous for other uses. In particular, some of the highly concentrated fluorocarbon emulsions of the present invention, when prepared with the appropriate surfactant, have been found to maintain substantial stability of both the partial pressure of oxygen ($pO_2$) and the partial pressure of carbon dioxide ($pCO_2$) through heat sterilization and room temperature storage for extended periods of time. Such stability is useful when using the fluorocarbon emulsions of the present invention as a fluid in calibrating instruments used for measuring, for example, the $pO_2$ and $pCO_2$. It is sometimes desired when using such instruments that such a fluid be biocompatible, so that should any of the fluid used in or with such an instrument later interact or pass on to a patient, there will be no danger of toxicity or injury to the patient or instrument.

Fluorocarbon emulsions can be oxygenated by way of several methods. One method found to be particularly useful is by placing the fluorocarbon emulsion into a pneumatically closed or closable container, and filling the space unoccupied by the emulsion with oxygen. This method takes advantage of the fact that the fluorocarbon and fluorocarbon emulsions by virtue of their low surface tension tend to form a film or layer on the inner surface of the wall of the container.

Figures 1, 2, 2A, 3, 3A:
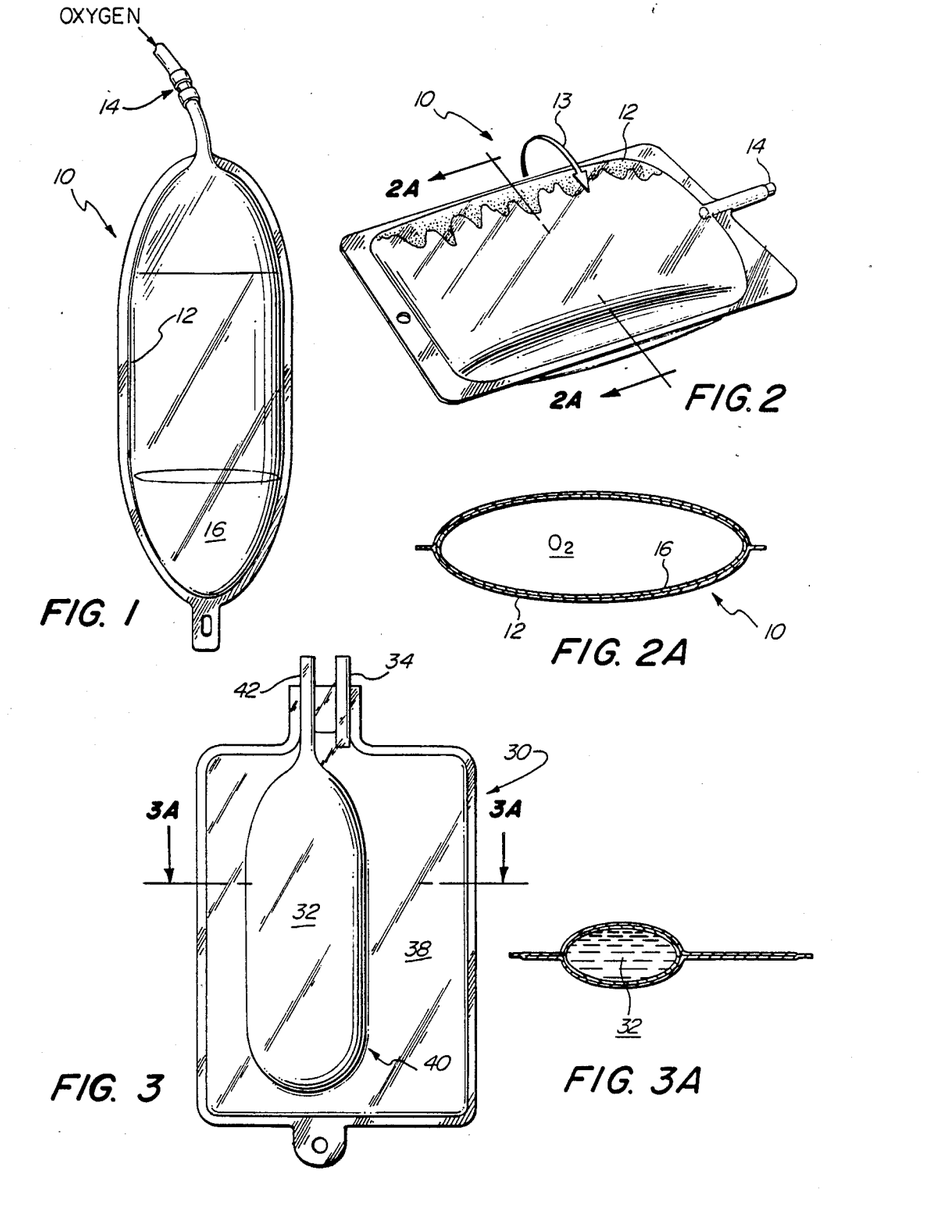
FIG. 1 is a front view of a flexible container having a portion cut away for clarity, and having a fluid fluorocarbon emulsion contained therein, showing a method of one aspect of an embodiment of the invention.
FIG. 2 is a perspective view of another step in the method shown in FIG. 1.
FIG. 2A is a cross-sectional view taken along line 2A—2A of FIG. 2 showing oxygenation of the fluorocarbon emulsion in accordance with the embodiment of the present invention shown in FIG. 1.
FIG. 3 is a cross-sectional view showing a two container system for oxygenating fluid fluorocarbon emulsion contained in one of the containers in accordance with an alternative embodiment of the present invention.

In one embodiment of this aspect of the invention, reference being had initially to FIGS. 1 and 2 of the accompanying drawings, the container is a flexible bag 10, having a wall 12 and an openable port or aperture 14 for inserting the oxygen into the bag 10. The port or aperture is, a Teflon coated butyl rubber stopper, made openable by penetration by or insertion of a hypodermic needle or tube. The bag 10 is collapsed onto the emulsion 16 contained therein. In this method, the emulsion fills approximately less than half of the volume of the bag 10 in a fully inflated condition. Oxygen is inserted to displace any inert gas in the emulsion and would fill out the bag 10, as shown in FIG. 1. As shown in FIG. 2, the longitudinal length of the bag 10 is oriented substantially horizontally and rotated or moved around so that the fluorocarbon emulsion 16 forms a film or coating on the inner surface of the wall 12, as better seen in FIG. 2A of the accompanying drawings. FIG. 2A is a cross-sectional view of the bag 10 of FIG. 1 taken approximately mid-length of its longitudinal dimension after the bag 10 has been rotated or moved about as described. The oxygen will dissolve easily into the fluorocarbon emulsion 16.

Another method for oxygenating the fluorocarbon emulsion involves a two bag or container system, one bag or container containing a gas permeable membrane or wall and being contained within the other. One of the containers is filled with the fluorocarbon emulsion, while the other is filled with oxygen. The oxygen diffuses through the membrane and dissolves in the emulsion. The gas permeable membrane is made preferably of a substantially pure silicone rubber.

One arrangement of such a system, reference being had to FIG. 3 of the accompanying drawings, comprises an outer bag 30 and a flexible inner bag 40 inserted within the outer bag 30. Fluorocarbon emulsion 32, such as is described herein, is contained within the inner bag 40. The outer bag 30 has a port or openable aperture 34, such as a Teflon coated butyl rubber stopper which is penetrable by a hypodermic needle or tube for insertion of gas or fluid, as will be described below. The outer bag 30 may be composed of polyvinylchloride, polyethylene or similar material. The inner bag 40 is defined by a gas permeable, but substantially fluorocarbon impermeable membrane 36, such as a substantially pure silicone rubber which is compatible with the emulsion 32 and which does not elute any potentially toxic substances into the emulsion 32 during long term storage, which may exist for months and longer. Initially, the outer bag 30 is essentially collapsed upon itself and upon the inner bag 40, but defines a variable space 38 between it and the inner bag 40 which increases as fluid or gas is inserted through the port 34. The inner bag 40 has a port or aperture 42 openable to the outside, such as a Teflon coated butyl rubber stopper penetrable by a tube or hypodermic needle as described above.

When it is desired to oxygenate the fluorocarbon emulsion 32, oxygen 44 is inserted into the outer bag 30 through the port 34 to inflate the bag 30 and occupy the space 38 and purge any nitrogen or other inert gas which may be used during storage to occupy space 38, and diffuses through the gas permeable membrane 36 to dissolve in the fluorocarbon emulsion 32 contained in the inner bag 40. Oxygenated fluorocarbon emulsion 32 can be extracted through port 42 after the oxygen 44 has dissolved into the emulsion 32.

Another method of oxygenating the fluorocarbon emulsion using substantially the same two-container apparatus, has fluorocarbon emulsion 32 inserted in the space 38 and the inner bag 40 substantially collapsed upon itself. The outer bag 30 surrounds the inner bag 40 which has port 42 as described above. The two bags 30, 40 define the space 38 between them. When oxygenation is desired, oxygen 44 is inserted into the inner bag 30 through the port 42.

The oxygen 32 may be under slight pressure to increase the rate of diffusion inwardly through the gas permeable bag membrane and into the fluorocarbon emulsion 32. Also, oxygen under pressure may be used where a $pO_2$ different than atmospheric may be desired or useful, such as, for example, in perfusions of the heart where oxygen bubbles would be metabolized fast.

Figure 4:
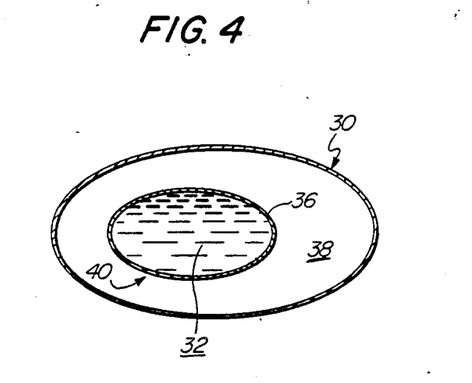
FIG. 4 is a cross-sectional view taken along line 4—4 of FIG. 3 showing oxygenating the fluorocarbon emulsion contained within one of the two containers.
Figure 5:
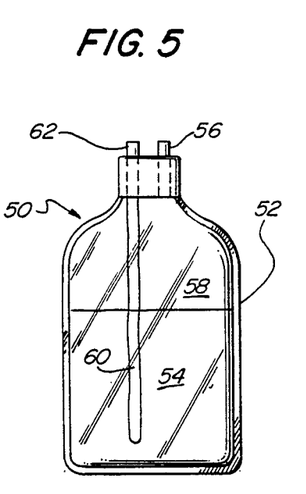
FIG. 5 is a cross-sectional view of a two container system showing yet another alternative embodiment of a method for oxygenating the fluorocarbon emulsion according to the present invention.

Alternatively, and presently preferred where long or extended storage is contemplated, the outer container could be a sealed glass bottle system 50 substantially inert with the fluorocarbon emulsion, as best seen in FIG. 5 of the accompanying drawings. The system 50 includes a sealed or glass bottle 52 containing a fluorocarbon emulsion 54 and a port or aperature 56 which is penetrable with a hypodermic needle or tube for extraction or insertion of fluid or gas. Initially, an inert gas such as nitrogen 58 fills the head space. Inside the bottle 52 is a flexible bag 60 defined by a gas permeable membrane as described above for the embodiments of FIGS. 3 and 4. The bag 60 has a port or aperature 62 penetrable by a hypodermic needle or tube for insertion of gas. The membrane of the bag 60 may be made of the silicone rubber as described for the emboidments of FIGS. 3 and 4 above. Alternatively, the bag 60 may also be substantially impermeable to the fluorocarbon emulsion.

Figure 6:
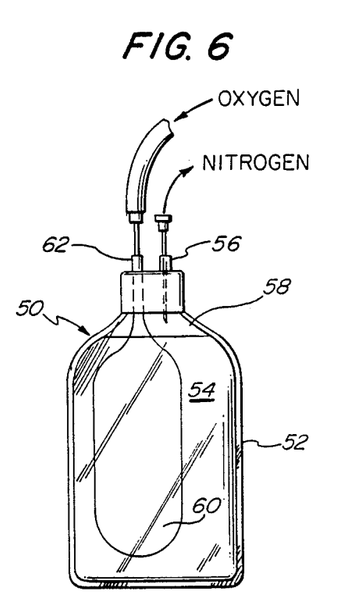
FIG. 6 is a cross-sectional view of the two container system of FIG. 5 showing oxygenation of the emulsion.

When oxygenation is desired, oxygen is inserted into bag 60 through port 62 to inflate the bag 60. The head space gas, nitrogen is forced through the port 56 and evacuated. The oxygen permeates the membrane of the bag 60 to dissolve into the fluorocarbon emulsion 54, as illustratively shown in FIG. 6 of the accompanying drawings. When oxygenated emulsion 54 is desired, it can be extracted through the port 56 by inverting the bottle 52.

The emulsions of the present invention may be made by a process that may be accomplished in several ways. Primarily, the preferred embodiment of the process envisages an impingement of a mixture of the fluorocarbon in the vehicle, which contains the surfactant and other ingredients of the emulsion, at high pressure and high momentum. One method could include a cavitation procedure, which could accomplish the desired emulsion characteristics of small particle size with maximum or most efficient use of the emulsifying agent. Other methods providing sufficient turbulence may also be employed.

Initially, it is contemplated that a vehicle, as that term is defined in my co-pending application Ser. No. 818,690, be prepared by mixing into an aqueous continuous phase, suitable buffering agents and osmotic agents in order to maintain the pH and the osmolality of the ultimate emulsion through sterilization and storage. Suitable osmotic agents include hexahydric alcohols such as, for examples, mannitol and sorbitol, certain sugars such as glucose, mannose and fructose, as well as glycerol, sodium chloride, and osmotic agents such as hydroxyethyl starch ("HES"), dextrans, gelatins and albumin. Suitable buffering agents include, for examples, imidazole, tris(hydroxymethyl)aminomethane, also known as Tham, sodium bicarbonate, monobasic potassium phosphate, dibasic potassium phosphate, monobasic sodium phosphate and dibasic sodium phosphate. Tham is also known as Trizma and is available from Sigma Chemical Company of St. Louis, Mo. Tham and imidazole do not precipitate calcium, and thus may be a desired buffer where calcium containing compounds are used in the emulsion or where the blood or emulsion might otherwise be exposed to calcium compounds. Imidazole may also be selected as a buffer in emulsions used to improve radiation treatments for, for example, a tumor because imidazole appears to sensitize the tumor to radiation and enhance the desired effects of the radiation to the tissue containing it. Imidazole may be used as a substitute buffer for phosphates, which appear to shield occupied tissue from the necrotic effects of radiation.

An emulsifying agent is included in the mixture. A common emulsifying agent is yolk lecithin, as it is known to be biocompatible. Lecithin, and generally those unsaturated phospholipids used as emulsifying agents, are normally subject to oxidation or attack by free oxygen as the oxygen seeks to bond with the double bonds within the lecithin molecule. The chemical changes may weaken the membranes of the emulsion particles or may form unacceptably high concentrations of fatty acids or lysolecithin or other oxidation or degradation products.

It has been found that these effects can be eliminated or reduced in the emulsions of higher fluorocarbon concentrations, that is on the order of 50% w/v or more, by having an oxygen resistent, saturated lecithin or lecithin analog as the emulsifying agent. Such lecithins include 1,2-dipalmitoyl-sn-glycero-3-phosphocholine and 1,2-dimyristoyl-sn-glycero-3-phosphocholine. Additional such saturated lecithins include a hydrogen saturated soy derived lecithin which, initially before hydrogenation, comprised 61.602% linoleaic residues, 18.297% palmitaic residues, 10.351% oleaic residues, 5.311% linolenaic residues, 4.117% stearaic residues, 0.17% palmitoleaic residues and 0.153% myristaic residues; and saturated hydrogenated yolk extract lecithins. Fluorocarbon emulsions having very good particle size stability, and having stable partial pressure of oxygen and partial pressure of carbon dioxide characteristics have been found without the need of an anti-oxidant and without the need of any other emulsifying agent.

It has been found advantageous to include in the emulsion a chelating agent to neutralize the effects of certain heavy metals. Certain metals, such as copper and iron, for example, catalyze oxidation and hydrolysis of lecithin. The addition of a sequestering agent, such as, for example, disodium calcium ethylenediaminetetraacetic acid ($Na_2Ca$ EDTA), in very small quantities can eliminate or reduce the oxidation effect of such heavy metal catalysts. Sequestering agent in the amount of as low as 0.005% w/v and as high as 0.04% w/v have been found to help in reducing the catalytic effects of the heavy metal on the oxidation of the lecithin, with the preferred amount being from approximately 0.01% w/v to 0.02% w/v.

Anti-oxidants, such as, for examples, tocopherol including alpha tocopherol acetate, mannitol or ascorbic acid optionally may be included in the mixture. Such anti-oxidants would not be necessary, or their use could be greatly reduced when using substantially fully hydrogen saturated synthetic phospholipids as suggested herein. It is possible to hydrogenated yolk lecithin and soybean derived lecithin, but such hydrogen saturated lecithin tend to be less fluid than unhydrogenated lecithin.

The vehicle mixture containing the surfactant has the fluorocarbon mixed thereinto. Preferably, the fluorocarbon is mixed in an even, measured rate to obtain the most efficient mixture. The fluorocarbon may be one of the fluorocarbons described hereinabove.

The resulting mixture is then forced at very high pressure into a flow path. The pressure should be sufficient to achieve high flow velocity to increase energy input to the mixture. In accordance with one aspect of the process invention, the flow is pumped at more than 10,000 pounds per square inch (psi) at a high flow rate through two flow paths which open into a cavity. Pressures of as low as 4,000 psi have been used with satisfactory results where the fluorocarbon concentration in the emulsion is lower, on the order of 10% to 25% w/v. The flow paths are directed so that the flows of the mixture from each path impinge upon each other within the cavity. The mixture then flows to strike a surface, and is removed from the cavity. It is believed that cavitation occurs in the mixture when it is directed from the flow path into the cavity.

Figure 7:
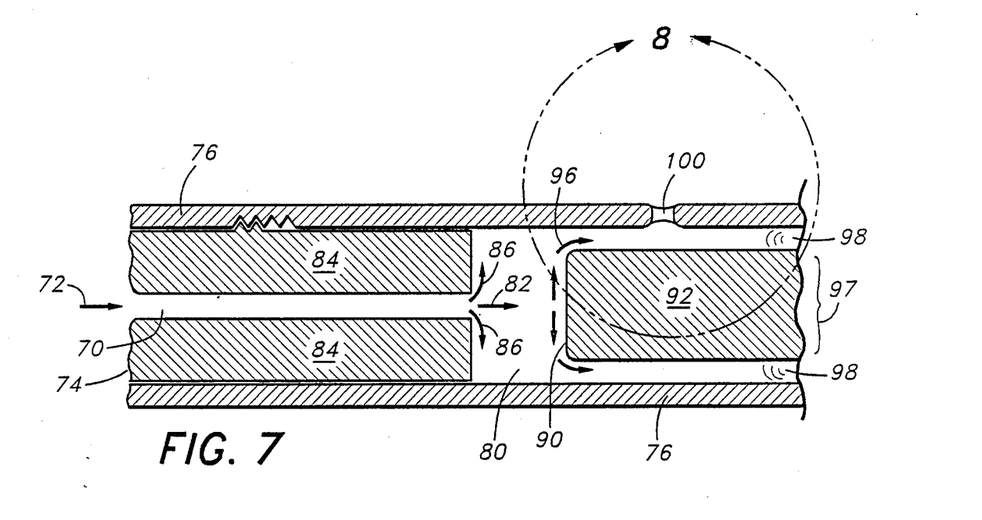
FIG. 7 is a cross-sectional view of method of manufacturing the fluorocarbon emulsion of the present invention.

In accordance with another embodiment of this aspect of the process invention, a single flow path 70 is provided, as shown in FIG. 7 of the accompanying drawings. The fluorocarbon mixture is forced in the direction of arrow 72 at 10,000 pis to 25,000 psi pressure through this flow path 70, which is defined by an axial vein through a cylindrical plug 74. The plug 74 fits within the inside of pipe 76. The fluorocarbon mixture exits the path 70 into cavity or chamber 80, as indicated by arrow 82. At the pressures indicated, the mixture expands upon entering cavity 80, and flows around the circular lip 84 in the direction of arrows 86 to cavitate, it is believed.

A great portion of the fluorocarbon mixture is forced forward and impinges, as indicated by the arrows 88, upon the surface 90 of the cylindrical plug 92, fixed within the pipe 76 at an anchor not shown.

Figure 8:
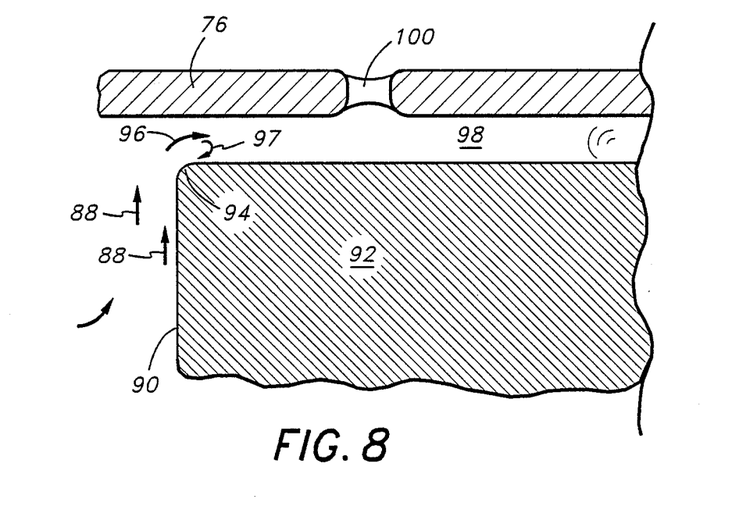
FIG. 8 is a portion of the cross-sectional view of FIG. 7 blown up for clarity.

The action of the mixture may be better understood by reference to FIG. 8 in conjunction with FIG. 7. FIG. 8 is a blow-up, partial cut-away of a section of the system of FIG. 7, showing the believed action of the mixture in greater detail. It is believed that the mixture flows radially from the center of the surface 90 of the plug 92, as indicated by the arrows 88. The mixture is forced in the direction of arrows 96 into the annular space 98 which is concentrically between the plug 92 and the pipe 76. It is believed that the mixture expands in the direction indicated by the arrows 97, and cavitates as it is forced pass the edge or lip 94 of the surface 90. The mixture is withdrawn from the system through port 100. The distance between the plug 74 and the surface 90 of the plug 92 can be adjusted as desired. Where the fluorocarbon concentration in the emulsion is lower, below 50% w/v for example, lower pressures may produce satisfactory emulsions. Pressures as low as 4,000 psi, will produce cavitation and provide some emulsification where the fluorocarbon is in the emulsion in the range of approximately 10% w/v to 25% w/v.

Some multiple runs or passes, three, four or more in accordance with the preferred embodiment of this invention, through such a procedure will increase the desired stability, decrease the particle size, and optimize the efficiency characteristics of the emulsion. Moreover, it has been found that the temperature of the emulsion rises during such procedures and methods as set forth herein. It is believed that the emulsion forms more reliably and results in an emulsion that is more stable in particle size, pH, osmolality, $pO_2$ and other characteristics when the temperature of the mixing and cavitation chambers or cavities are maintained cool, as with an ice or a water bath for examples. When hydrogenated lecithin or synthesized lecithins are used, the emulsion is manufactured, for example, in a cavity which is being cooled by a water bath maintained at from 15 degrees C. to 22 degrees C.

The invention can be better understood by way of the following examples which are representative of the preferred embodiments thereof:

EXAMPLE I

A one liter batch of emulsion made in accordance with the procedure described above, contained perfluorooctylbromide (PFOB) at 90% w/v, yolk derived lecithin at 4.5% w/v, suitable non-calcium precipitating buffering agent, Tham at 0.05% w/v, suitable osmotic agent at 0.5% w/v, $CaCl_2$ 0.015% w/v and $MgSO_4$ at 0.003.% w/v as buffering to control the pH, alpha-tocopherol acetate at 0.05% w/v and NaCl at 0.378% w/v, and a quantity sufficient of water ($H_2O$). In particular, the lecithin, Tham, osmotic agent, $CaCl_2$, $MgSO_4$, alpha-tocopherol acetate, NaCl and water were mixed together, forming the vehicle. The perfluorooctylbromide was mixed evenly into the vehicle. The result was forced at 14,000 psi pressure into two flow paths which were re-directed towards each other in a cavity, and the resultant was withdrawn. The passage through the two flow paths and into the cavity was repeated four times. This emulsion was oxygenated before use by placing approximately 65 milliliters (ml) in a 500 millimeter plastic, flexible bag. Nitrogen was removed and the bag was expanded by injecting 100% oxygen to achieve a partial pressure of oxygen ($PO_2$) of 653 Torr in the emulsion. The bag was turned around so that the emulsion formed a relatively thin film on the inside surface of the wall of the bag, allowing the oxygen to dissolve into the fluorocarbon more readily.

A catheter was inserted in the left anterior descending (LAD) coronary artery of a dog and the oxygenated emulsion was perfused through it at a rate of 24 ml/minute. Mean coronary pressure was 80 millimeters (mm) mercury (Hg). During the two minute perfusion, there was a normal contraction of the heart muscle fed by the left anterior descending coronary artery. Contractility was measured precisely with two ultrasonic dimension crystals embedded in the heart muscle on both sides of the left anterior descending coronary artery. At the end of the two minute perfusion, the artery was perfused with the dog's own blood, and the heart muscle continued to contract in the normal fashion with no cardiac arrythmia as measured by the electrocardiogram. The mean coronary artery pressure was 110 mm Hg. during the blood perfusion.

Upon observation by X-ray radiography, the radiodensity was good with the emulsion in the artery being at least as discernible or perceptible as the image obtained with a 50% dilution of Hypaque Sodium 50%, a known iodine contrast agent available from Winthrop Pharmaceuticals, New York, NY.

The heart of the dog tolerated the perfusion well judging by the observations that heart contractility and rhythm were as good during perfusion with the PFOB as with blood. The coronary vascular resistance was lower during perfusion with the PFOB emulsion than with the dog's own blood. In particular, the wall motion, i.e. heart contraction was normal during the two (2) minute PFOB perfusion, as seen from the following Table. The results of the perfusion using the emulsion of the present invention were compared with the results of a similar perfusion of similar dogs using whole blood from the dogs themselves. All measurements in the Table below are the mean of measurements of five dogs. In this Table, HR represents the heart rate in beats per minute, EDL represents end-diastolic length in millimeters (mm), %DL represents segment shortening, and AoSP represents aortic systolic pressure in mm Hg.:

TABLE I

| | Control | End of Perfusion | 5 min. after |
|---|---|---|---|
| Blood of the dogs: | | | |
| HR | 116 ± 15 | 114 ± 17 | 118 ± 14 |
| EDL | 13.7 ± 2.2 | 14.1 ± 2.2 | 13.3 ± 2.1 |
| % DL | 17.8 ± 3.3 | 14.5 ± 4.8 | 19.1 ± 5.3 |
| AoSP | 127 ± 33 | 132 ± 26 | 124 ± 30 |
| PFOB Emulsion: | | | |
| HR | 115 ± 11 | 113 ± 11 | 112 ± 11 |
| EDL | 12.8 ± 2.4 | 13.7 ± 2.7 | 12.9 ± 2.4 |
| % DL | 21.2 ± 5.1 | 22.8 ± 1.4 | 18.0 ± 5.1 |
| AoSP | 116 ± 21 | 111 ± 23 | 110 ± 24 |

EXAMPLE II

A batch was prepared having 125% weight per volume of mono-brominated perfluorocarbon ($C_8F_{17}Br$), 0.03% weight per volume of Tham, a suitable buffer to maintain pH, 0.4% weight per volume of mannitol, 0.2% weight per volume of NaCl, a quantity sufficient of water, with a soy lecithin as an emulsifying agent at 3.5% weight per volume. The soy lecithin was hydrogenated, that is to say, substantially all of the double bonds on the fatty acids were saturated with hydrogen.

The emulsion was equilibrated with 100% oxygen during formulation and bottled with 100% oxygen in the remaining space. The emulsion was then sterilized by autoclave at 121 degrees C. for eight (8) minutes. Fifteen (15) hours after sterilization and storage at room temperature, $pCO_2$ and $pO_2$ were measured as $pCO_2=0.3$ mm Hg, and $pO_2=810$ mm Hg., where the barometric pressure was 748 mm Hg.

The mean particle size was measured on the Nicomp submicron particle sizer manufactured by Pacific Scientific Co. of Anaheim, CA. This analyzer determines relative quantities of various sized particles by a method of dynamic light scattering. Results are given digitally as shown, for example, in examples given in my co-pending application Ser. No. 818,690 referenced hereinabove. Before sterilization, the mean particle size was measured at 311 nanometers (nm), with the particle size distribution showing a Gaussian curve. After sterilization by autoclave at 121 degrees C. for eight minutes and 15 psi, the mean particle size measured 361 nm. After an additional autoclave heat sterilization performed for 60 minutes at 211 degrees C., the mean particle size measured 358 nm.

To determine its biocompatibility, this emulsion was injected intravenously in six rats in a dose of 4 gm. fluorocarbon per kg. of body weight. Six additional rats were injected with a comparable amount, that is 4 ml/kg. of normal saline for comparison purposes. One week after injection, the rats receiving the fluorocarbon emulsion had showed a mild, transit anemia, 0.95 hemoglobin concentration as compared with control rats injected with normal saline, but otherwise had blood characteristics comparable to those of the control rats. The fluidity or viscosity of the emulsion was, therefore, biocompatible for injection in the blood vessels in the body.

EXAMPLE III

A batch was prepared having 100% weight per volume of mono-brominated perfluorocarbon ($C_8F_{17}Br$), 0.03% weight per volume of Tham, a suitable buffer to maintain pH, 0.4% weight per volume of mannitol, 0.2% weight per volume of NaCl, a quantity sufficient of water, with a soy lecithin as an emulsifying agent at 6% weight per volume. The lecithin was not saturated with hydrogen, that is to say the carbon double bonds were not saturated with hydrogen. The emulsion was saturated with oxygen during formulation or manufacture. The oxygen attacks the non-hydrogenated doublebonds, oxidizing the lecithin. Measurements taken after twelve days revealed a decrease in the $pO_2$ from 359 mm Hg to approximately 4.5 mm Hg, and an increase in the $pCO_2$ from 1.8 mm Hg to approximately 8.5 mm Hg.

A comparison of the $pO_2$ and $pCO_2$ measurements after set time periods of the emulsion of Example II with that of Example III, shows that the hydrogenated lecithin allows for a stable oxygenation, while the emulsion with a lecithin that is not saturated with hydrogen suffers rapid oxidation in the presence of oxygen:

TABLE II

|  | 15 hours | | 12 days | | 32 days | |
| --- | --- | --- | --- | --- | --- | --- |
|  | $pO_2$ | $pCO_2$ | $pO_2$ | $pCO_2$ | $pO_2$ | $pCO_2$ |
| Ex. III (H) | 810 | 0.3 |  |  | 787 | 0.1 |
| Ex. IV | 359 | 1.8 | 4.5 | 8.5 | 0 | 12.2 |

EXAMPLE IV

A fluorocarbon emulsion was prepared having 102.5% perfluorodecalin, 4.5% weight per volume of lecithin, 0.05% w/v of an anti-oxidant, 1.2% weight per volume of mannitol to assist in osmolality and anti-oxidation, 0.036% w/v of Tham as a buffer, and water in quantity sufficient to form the emulsion. The emulsion was made by mixing at a substantially steady, even rate the fluorocarbon into the vehicle, which comprised the remaining ingredients. The resultant mixture was passed through a flow path at a high pressure, 17,000 psi, and divided into two flow paths which were directed to impinge upon each other in a cavity into which the flow paths are directed. The procedure was repeated through five passes. The emulsion had good fluidity and presented no viscosity problem.

Before sterilization, the emulsion's particle sizes were measured using the Nicomp particle sizer as described above in Example II, and the mean particle size was measured at 180 nm. Twenty-four (24) hours after heat sterilization in an autoclave at 121 degrees C. for eight minutes, the mean particle size was measured at 225 nm. The osmolality was 258. The pH varied only by 0.02 from before and after sterilization.

The emulsion was then subjected to a series of freeze and thaw cycles where the emulsion was first frozen rapidly to a temperature of approximately minus (−) 20 degrees C. Then the frozen emulsion was thawed at ambient temperatures on the order of 17 degrees C. to 21 degrees C. The cycle was then repeated after storage of the emulsion at ambient or room temperatures, on the order of 17° to 21° degrees C. for at least 180 minutes between each cycle. The freeze-thaw cycle has been described, and is frequently used as a test that accelerates shelf life and other time related storage stresses for emulsions. See, for example, *Advances in Clinical Nutrition* at pages 228–229, I. D. A. Johnston, ed., (1982) published by MTP Press Limited of Boston, MA.

EXAMPLE V

An emulsion having substantially the same composition as set forth in Example IV above, except that the fluorocarbon is 100% w/v F-44E, was prepared using the procedure including the heat sterilization as set forth in Example IV. Mean particle size measurements were taken using the same analyzer as set forth in Example IV, and the results are set forth in Table III below. The pH decreased only by 0.10 from before sterilization until 24 hours after sterilization. The emulsion formed had good fluidity and presented no viscosity problem.

EXAMPLE VI

An emulsion having substantially the same composition as set forth in Example IV above, except that the fluorocarbon is 100% w/v F-2-butyltetrahydrofuran ("RM-101" or "FC-75") was prepared using the procedure including the heat sterilization as set forth in Example IV. Mean particle size measurements were taken using the same analyzer as set forth in Example IV, and the results are set forth in Table III below. The pH decreased only by 0.08 from before sterilization until 24 hours after sterilization. The emulsion formed had good fluidity and presented no viscosity problem.

EXAMPLE VII

An emulsion having substantially the same composition as set forth in Example IV above, except that the fluorocarbon is 100% w/v F-66E. Mean particle size measurements were taken using the same analyzer as set forth in Example IV, and the results are set forth in Table III below. The emulsion formed had good fluidity and presented no viscosity problem.

The mean particle sizes before sterilization, after sterilization and immediately after each of several freeze-thaw cycle tests for these emulsions are given in the following Table IV, where the numbers in the row entitled "PreSter" represent the mean particle size measured immediately prior to sterilization; the numbers in the row entitled "PostSter" represent the mean particle sizes after sterilization by autoclave at 121 degrees C. for eight (8) minutes, the numbers in the rows entitled "1st F-T", "2nd F-T" and "3rd F-T" represent the mean particle sizes measured after the respectively numbered freeze-thaw cycle ("F-T"):

TABLE III

|  | Decalin (Ex. IV) | F-44E (Ex. V) | Rm101 (Ex. VI) | F-66e (Ex. VII) |
| --- | --- | --- | --- | --- |
| PreSter | 180 | 167 | 135 | 188 |
| PostSter | 225 | 225 | 209 | 189 |
| 1st F-T | 299 | 276 | 266 | 198 |
| 2nd F-T | 280 | 264 | 255 | 200 |
| 3rd F-T | 301 | 287 |  | 194 |

EXAMPLE VIII

An emulsion having substantially the same composition as set forth in Example IV above, except that the fluorocarbon is 100% w/v $C_8F_{17}C_2H_5$ ("F-octylethylhydride"). Mean particle size measurements were taken using the same analyzer as set forth in Example IV. The pH decreased only by 0.12 from before sterilization until 24 hours after sterilization. The emulsion formed had good fluidity and presented no viscosity problem.

EXAMPLE IX

To ascertain particle size stability over extended periods of time in a high concentration fluorocarbon emulsion, a batch of 100% weight per volume of perfluorooctylbromide (PFOB) was prepared, using the method or procedure set forth in the application Ser. No. 818,690. Specifically, an amount of yolk derived lecithin was mixed into an aqueous phase such that the amount of lecithin in the ultimate emulsion was 6% weight per volume. Sodium phosphates were added as a buffer to maintain pH level, and sodium chlorides were added to maintain desired osmolality. An amount of alpha-tocopherol acetate was added, to limit oxygen degradation of the lecithin. Water was added in a quantity sufficient for the composition. An amount of perfluorooctylbromide was introduced into the mixture at a measured rate, and the mixture was forced through a flow path into an impingement chamber or cavity under 15,000 pounds per square inch of pressure. The flow path was of the type that divided the flow into two paths, and directed the flows at each other within impingement cavity. Four passes were made through the cavity.

The emulsion was then sterilized by autoclave at 121 degrees C. for 15 minutes. The sterilized emulsion was then stored at room temperatures which ranged during the trial from 15 degrees to 30 degrees C. The average particle size was measured using a Nicomp particle analyser, as described in Example III above. The mean particle size was measured initially after sterilization as 239 nm, at one month as 262 nm, at four months as 252 nm, and at ten months as 209 nm, thus indicating a very substantial particle size stability notwithstanding the high concentration of the emulsion and the low concentration of the surfactant. The fluidity, or lack of viscosity was suitable for use of the emulsion intravascularly in humans with no adverse toxicity.

EXAMPLE X

A 10 liter batch of 100% perfluorooctylbromide emulsion as described for Example IX above was kept at a different location. The emulsion was sterilized by autoclave at 121 degrees C., but for eight minutes. The emulsion was then stored at ambient temperatures which were maintained substantially at from 15 degrees to 30 degrees C. Mean particle size measurements were taken at various times after sterilization, as follows: At sterilization, 265 nm; at one month, 270 nm; and, at eight months, 251 nm. Again, the mean particle size measurement appeared stable at room temperature for substantial and extended periods of time. The emulsion was used intravascularly in humans satisfactorily using doses of 3 gm. of fluorocarbon per kg. of body weight.

EXAMPLE XI

The emulsion of Example IV above was injected into the tail vein of four (4) Sprague-Dawley rats at a rate of 2 ml/kg/min. until a total amount of 10 gm. of fluorocarbon per kg. of body weight was injected. Four (4) rats were treated with the same protocol, but were injected with a normal physiological saline solution, instead of the emulsion, as a control group. The rats receiving the emulsion were observed and blood samples were taken and the blood hematology and chemistry were analyzed during injection, at seven days and at fourteen days. The rats showed a mild anemia at 14 days, but otherwise exhibited generally good health during observations and in the analyses.

EXAMPLE XII

The emulsion of Example V above was injected into the tail vein of four (4) Sprague-Dawley rats at a rate of 2 ml/kg/min. until a total amount of 10 gm./kg. of the fluorocarbon of body weight was injected. Four (4) rats were treated with the same protocol, but were injected with a 0.9% saline solution, instead of the emulsion, as a control group. The rats receiving the emulsion were observed and blood samples were taken and analyzed during injection and at seven days and at fourteen days. The rats exhibited good health during observations and in the analyses, having a mild anemia noticed at seven and at fourteen days.

EXAMPLE XIII

The emulsion of Example I above, having 100% weight per volume PFOB, 6% weight per volume yolk lecithin, was injected into the inferior vena cava veins of five (three female, two male) mongrel dogs. Injections of the fluorocarbon emulsion were alternated with injections of Renografin-76 ("R-76"), a known ionic iodinated contrast agent having a high (2188) osmolarity, commercially available from Squibb & Co. of New Brunswick, NJ. in order to ascertain the validity of the dog model. Both the fluorocarbon emulsion and the R-76 were injected at the rate of 20 cc/sec. until a total volume of 1 cc/kg. of the dog's body weight was injected. The injections were spaced apart by a period of from 45 minutes to 60 minutes to allow the readings of the measurements to return to a baseline. Readings of the left ventricular end systolic pressure (LVESP) and the aortic flow (AoFlow) were taken immediately prior to, and at 0.2, 0.3, 0.5 and 0.8 of a minute, and at 1, 2, 5, 15 and 30 minutes after injection. Three dogs received a fluorocarbon emulsion injection, followed by a R-76 injection, followed by a fluorocarbon emulsion injection. The other two dogs receive a R-76 injection, followed by a fluorocarbon emulsion injection and then followed by a R-76 injection. Readings were taken continuously and compared with its standard and read as a percent change. The average percent change for the left ventricular end systolic pressure (LVESP) and the aortic flow (AoFlow) resulting from the PFOB emulsion injection and resulting from the R-76 injection for the most significant times of reading are shown in the following Table V:

TABLE V

| Time (min.) | Average Percent of Change | | | |
|---|---|---|---|---|
| | LVESP | | AoFlow | |
| | PFOB Eml. | R-76 | PFOB Eml. | R-76 |
| 0.2 | 0.7 | 4.1 | −3.6 | 6.6 |
| 0.3 | −2.6 | −5.5 | 1.3 | 18.9 |
| 0.5 | 0.5 | −16. | 2.3 | 31.5 |
| 0.8 | 1.2 | −8.9 | −0.3 | 26.6 |
| 1.0 | 1.2 | 1.3 | 1.3 | 19.1 |
| 2.0 | −2.6 | 3.8 | 1.6 | 15.5 |
| 5.0 | −2.5 | 5.0 | 0.8 | 14.9 |
| 15.0 | 3.6 | −0.2 | 0.9 | 6.8 |
| 30.0 | 1.7 | 2.7 | 0.7 | 1.5 |

Immediately following the administration of the R-76 agent, the left ventricular end systolic pressure decreased noticably, and the aortic flow increased noticably. The left ventricular end systolic pressure and the aortic flow had no comparable or significant change or variation following the injections of the PFOB emulsion.

EXAMPLE XIV

A fluorocarbon emulsion was prepared in accordance with the procedures set forth in this invention, comprising 100% w/v F-decalin, 9% w/v lecithin, 1% w/v mannitol, 0.05% w/v of tocopherol and 0.0247% w/v of Tham. The emulsion was injected into the tail vein of 6 rats for a total amount of fluorocarbon of 10 gm./kg. of body weight. At one week, the liver and spleen were examined and found to be normal except for an enlargement resulting from some storage of the fluorocarbon in the liver and spleen.

EXAMPLE XV

A fluorocarbon emulsion was prepared in accordance with the procedures set forth in this invention, comprising 100% w/v F-44E, 9% w/v lecithin, 1% w/v mannitol, 0.05% w/v tocopherol and 0.0247% w/v of Tham. The emulsion was injected into the tail vein of 6 rats for a total amount of fluorocarbon of 10 gm./kg. of body weight. At one week, the liver and spleen were examined and found to be normal except for an enlargement resulting from some storage of the fluorocarbon in the liver and spleen.

EXAMPLE XVI

An emulsion of 100% weight per volume of perfluoroctylbromide was prepared substantially according to the procedure described above for Example I. The emulsifying agent comprised 4.5% weight per volume of a soy derived lecithin fully saturated with hydrogen. A sparge of oxygen was commenced at the beginning of the mixing procedure, beginning with the aqueous phase and continuing until the steps forcing the fluid into the flows. The prepared emulsion was further sparged with oxygen in the bottle containing the emulsion during storage. The emulsion was placed in a sealed container and sterilized by autoclave at 121 degrees C. for eight minutes. Measurements of the partial pressure of oxygen (pO$_2$) were taken at fifteen hours, seventy-two hours and three weeks after sterilization, and are set forth in Tables VI and VII below.

EXAMPLE XVII

An emulsion of 100% weight per volume of perfluorooctylbromide was prepared substantially according to the procedure described above for Example I. The emulsifying agent comprised 4.5% weight per volume of a fully synthetic lecithin, dimyristoyl phosphatidylcholine, fully saturated with hydrogen. A sparge of oxygen was commenced at the beginning of the mixing procedure, beginning with the aqueous phase and continuing until the steps forcing the fluid into the flows. The prepared emulsion was further sparged with oxygen in the container containing the emulsion during storage. The emulsion was placed in a sealed container and sterilized by autoclave at 121 degrees C. for eight (8) minutes. Measurements of the partial pressure of oxygen (pO$_2$) were taken at two and five days after sterilization, and are set forth in Tables VI and VII below.

EXAMPLE XVIII

An emulsion of 100% weight per volume of perfluoroctylbromide was prepared substantially according to the procedure described above for Example I. The emulsifying agent comprised 4.5% weight per volume of a fully synthetic lecithin fully saturated with hydrogen, dimyristoyl phosphatidylcholine. A partial sparge of nitrogen was commenced at the beginning of the mixing procedure, beginning with the aqueous phase and continuing until the steps forcing the fluid into the flows. The prepared emulsion in its storage container was further sparged with a low flow of nitrogen to provide a partial pressure of oxygen less than ambient but greater than zero for use as a calibrant for blood gas analysers. The emulsion was placed in a sealed container and sterilized by autoclave at 121 degrees C. for eight minutes. Measurements of the partial pressure of oxygen (pO$_2$) were taken at two and five days after sterilization, and are set forth in Tables VI and VII below.

EXAMPLE XIX

An emulsion of 125% weight per volume of perfluoroctylbromide was prepared substantially according to the procedure described above for Example I. The emulsifying agent comprised 3.5% weight per volume of a soy derived lecithin fully saturated with hydrogen. A sparge of oxygen was commenced at the beginning of the mixing procedure, beginning with the aqueous phase and continuing until the steps forcing the fluid into the flows. The prepared emulsion was further sparged with oxygen in the container containing the emulsion during storage. The emulsion was placed in a sealed container and sterilized by autoclave at 121 degrees C. for eight (8) minutes. Measurements of the partial pressure of oxygen (pO$_2$) were taken at fifteen hours, seventy-two (72) hours and three weeks after sterilization, and are set forth in Tables VI and VII below.

The measurements of the partial pressure of oxygen (pO$_2$) and of the partial pressure of carbon dioxide (pCO$_2$) are given in Tables VI and VII below, where all results are in mm Hg.:

TABLE VI

| | (pO$_2$) | | | |
|---|---|---|---|---|
| | Ex. XVI | Ex. XVII | Ex. XVIII | Ex. XIX |
| 15 Hr. | 823 | | | 810 |
| Day 2 | | 479 | 81.8 | |
| 72 Hr. | 773 | | | 753 |
| Day 3 | | 503 | | |
| Day 5 | | 475.1 | 77.6 | |
| 3 Wks. | 807 | | | 723 |

TABLE IV

| | (pCO$_2$) | | | |
|---|---|---|---|---|
| | Ex. XVI | Ex. XVII | Ex. XVIII | Ex. XIX |
| 15 Hr. | 0.05 | | | 0.05 |
| Day 2 | | 0.1 | 0.2 | |
| 72 Hr. | 0.05 | | | 0.05 |
| Day 3 | | 0.2 | | |
| Day 5 | | 0.0 | 0.0 | |
| 3 Wks. | 0.2 | | | 0.1 |

The tables indicate that the emulsions held the oxygen dissolved before sterilization where the lecithin is fully saturated with hydrogen, and that the carbon dioxide by-product of oxidation was not observed, or was very minor and inconsequential.

EXAMPLE XX

A 100% perfluorooctylbromide emulsion was prepared according to the method process described in Example I above, making four passes through the pressurizing and flow step. The emulsion resulted in 100% weight per volume perfluorooctylbromide, 6% weight per volume yolk lecithin, 0.05% weight per volume alpha tocopherol acetate, 0.024% weight per volume Na$_2$HPO$_4$ and 0.114% weight per volume NaH$_2$PO$_4$.

The emulsion was sterilized by autoclave at 121 degrees C. for eight minutes, and then stored at temperatures from 5 to 10 degrees C., for approximately ten (10) months. Furthermore, the emulsion was shipped back and forth overseas by airplane transportation without temperature control or special handling instructions, where the total transit time was at least two weeks. The emulsion was diluted after storage and just prior, to use to a fluorocarbon concentration of 50% weight per volume PFOB with a solution of salts and human albumin, as follows: In the final emulsion as diluted, the amount of albumin was 2.00% w/v, NaCl was 0.39% w/v, KCl was 0.02% w/v, $MgCl_2$ was 0.015% w/v, $CaCl_2$ was 0.020% w/v and $NaHCO_3$ was 0.18% w/v. The lecithin resulted in 3% w/v, or generally half of the original emulsion as prepared.

The diluted emulsion was used in an exchange transfusion where three OFA rats had their blood removed while the diluted emulsion was injected until the hematocrit was approximately 3%. The perfusion technique used was that described by Goodin, et al., 245 *American Journal of Physiology*, at pp. H519–23 (1983). Generally, the rats were anesthetized and a double lumen polyethylene catheter was inserted into the right jugular vein. After recovery from the anesthesia, the rats were placed into an atmosphere enriched with 60% fixed inspired oxygen ($FiO_2$) (as compared with ordinary atmosphere oxygen content of 20.9%). Blood was removed through one lumen of the catheter while a comparable amount of the emulsion was administered through the other.

The oxygen enrichment of the inspired atmosphere was reduced to 50% on the second day, 40% on the third day and 30% on the fourth day. The rats were returned to ordinary atmosphere on the fifth day. The rats successfully survived the experiments. These oxygen enriched atmospheres are compared with, for example, 20% w/v Fluosol-type fluorocarbon emulsions which required a 95% oxygen environment, which result sometimes in oxygen toxicity.

These results indicate that a fluorocarbon emulsion with a high concentration of fluorocarbon can be sterilized and stored at ambient or room temperatures for extended periods, even shipped through conventional transportation without special handling and remain highly stable, retaining a high capability of oxygen absorption so that the oxygen enrichment of the atmosphere can be kept low. Low oxygen enrichment is desirable because it eliminates the risk of oxygen toxicity, and permits the subject to breathe room air early after or during treatment. It may be difficult to supply oxygen enrichment of the atmosphere breathed in some situations such as, for example, during battle or in mass casualities.

EXAMPLE XXI

A contrast enhancing emulsion was formulated comprising 100% weight per volume perfluorooctylbromide, a single emulsifying agent comprising 4.5% weight per volume of yolk phospholipid with osmotic and buffering agents in quantity sufficient to balance the emulsion. The kidney, as well as the abdominal aorta, inferior vena cava and portal vein of a dog were imaged using a color flow Doppler effect technique before any administration of the emulsion. The emulsion was then administered intravenously to the dog, and an identical color flow Doppler effect imaging procedure was followed within 20 minutes after administration, to image the tissue indicated. The presence of the perfluorooctylbromide emulsion greatly enhanced the vascular images of the kidney. Blood vessels which were only faintly visible before the emulsion was administered, were more clearly visible and, further, more of blood vessels were imaged. Low velocity venous flow patterns which were difficult or impossible to image without a contrast medium, were distinguished so that streamlining of flow and layering of the emulsion were visible in the vena cava and portal vein after administration of the emulsion. It was concluded that the administration of the perfluorooctylbromide increased the sensitivity of the Doppler effect imaging technique, resulting in the imaging of smaller blood vessels and imaging of blood having slower flow velocity.

EXAMPLE XXII

Two batches of 500 ml each of an emulsion of perfluorooctylbromide were prepared having a composition of 100% w/v PFOB, 4.5% yolk derived lecithin, 0.036% w/v of a non-calcium buffer and 0.3447% w/v of an osmotic agent. In addition, in one of the two batches disodium calcium edetate ($Na_2Ca$ EDTA) in amount of 0.015% w/v was included. Both batches were prepared in accordance with the procedure of Example I above, with the $Na_2Ca$ EDTA included in the vehicle of one. Each batch was divided into four approximately equal parts. In each batch, the first and second parts had 5 micromoles per liter of cuprous chloride ($CuCl_2$) added as a control trace amount of heavy metal. In each batch, the first and third parts were sparged with nitrogen, while the second and fourth parts were oxygenated, that is had the nitrogen substantially replaced with oxygen. All parts were then sterilized by autoclave at 120 degrees C. for 30 minutes, and were observed at approximately 48 hours after autoclave. In the batch having the $Na_2Ca$ EDTA added, the color initially was white. In the batch having no $Na_2Ca$ EDTA added, the color initially was slightly off-white.

The first part of the batch not having the $Na_2Ca$ EDTA, having the nitrogen sparge but no copper added, showed a mild discoloration. The $pO_2$ increased from 14.7 mm to 17.4 mm Hg., the pCO increased from 3.0 mm to 4.65 Hg., and the pH dropped 0.60. The comparable first part of the batch having the $Na_2Ca$ EDTA in the emulsion, a nitrogen sparge but no copper added showed no discoloration, that is the emulsion remained white. The $pO_2$ increased from 9.7 mm to 20.8 mm Hg, the $pCO_2$ increased from 3.0 to 3.4 mm Hg., and the pH dropped approximately 0.36.

The second part of the batch not having the $Na_2Ca$ EDTA, being oxygenated but having no copper added, showed a severe discoloration, that is was dark tan. The drop in the pH was 3.25, the $pO_2$ decreased 31.4% and the $pCO_2$ increased 230%, indicating that oxidation was taking place. The comparable second part of the batch having the $Na_2Ca$ EDTA in the emulsion, showed a very slight discoloration, that is, it became slightly off-white, having a slight drop in the pH of 0.38, a decrease of $pO_2$ of only 0.2%, and a rise in the $pCO_2$ of from 2.6 mm Hg. to 3.0 mm Hg. The changes in the $pO_2$ and $pCO_2$ having the $Na_2Ca$ EDTA were within normal error of measurement.

The third part of the batch not having the $Na_2Ca$ EDTA, having the nitrogen sparge and having copper added, showed a mild discoloration, that is the emulsion became more off-white, having a drop in pH of 0.88.

The $pO_2$ increased from 18.2 mm to 29.5 mm Hg., and the $pCO_2$ increased from 2.8 mm to 5.1 mm Hg. The comparable third part of the batch having the $Na_2Ca$ EDTA in the emulsion, showed no discoloration. The color was white, the $pO_2$ increased from 8.5 mm to 11.7 mm Hg., the $pCO_2$ increased from 2.5 mm to 2.8 mm Hg., and the pH dropped 0.267.

The fourth part of the batch not having the $Na_2Ca$ EDTA, being oxygenated but having copper added, showed a moderate discoloration, that is, it became tan in color, having a drop in pH of 3.25, a decrease in the $pO_2$ of 41%, an increase in the $pCO_2$ of 203%, or 6.3 mm Hg, indicating that oxidation had occurred. The comparable fourth part of the batch having the $Na_2Ca$ EDTA in the emulsion, showed a slight discoloration, that is, it was off-white. The pH dropped 0.38, the $pO_2$ decreased 7.5% and the $pCO_2$ increased by 0.4 mm Hg.

A fluorocarbon emulsion having $Na_2Ca$ EDTA in the emulsion successfully chelates or sequesters trace amounts of copper and other heavy metals so as to neutralize the effect of such heavy metals on the oxidation of the emulsion.

The foregoing detailed description of my invention and of preferred embodiments thereof, as to products, compositions and processes, is illustrative of specific embodiments only. It is to be understood, however, that additional embodiments may be perceived by those skilled in the art. The embodiments described herein, together with those additional embodiments, are considered to be within the scope of the present invention.

I claim:

1. A method of dissolving a gas in a fluorocarbon emulsion comprising:
    a. providing a first flexible container that is permeable to gas, but not to liquids or solids, in contact with the interior of a second container, said first and said second containers having means for introducing and removing fluid;
    b. providing a fluorocarbon emulsion in one of said containers;
    c. inserting said gas to be dissolved into the other of said containers and allowing the gas to permeate said one container to provide an oxygenated fluorocarbon emulsion in said one container.

2. The method of claim 1, wherein said first container is substantially impermeable to said fluorocarbon emulsion.

3. The method of claim 1 wherein said gas is oxygen.

4. The method of claim 1 wherein said fluorocarbon emulsion is inserted in said first container.

5. The method of claim 1 wherein said second container is flexible, and is substantially collapsed upon said first container until said gas is inserted into said second container.

6. The method of claim 1 wherein the first flexible container is inserted into the second container, wherein said second container is compromised substantially of glass, said first and second containers defining a space between them, and wherein the fluorocarbon emulsion is inserted into said space in an amount less than the amount of space, and wherein said first flexible container is initially empty of content, comprising the further steps of:
    a. sparging the space remaining after insertion of the fluorocarbon emulsion with a second gas substantially inert to the emulsion; and
    b. inserting the first gas to be dissolved into said emulsion, into said first container to expand said first container and force second gas out of said second container, allowing said first gas to permeate said space to provide an oxygenated fluorocarbon emulsion in said space.

7. A method of dissolving a first gas in a fluorocarbon emulsion comprising:
    a. inserting a first flexible container that is permeable to said first gas into a second container comprised of substantially rigid glass, said first and said second containers having selectively penetrable ports for holding fluid inside said container, said first and said second containers defing a space between them;
    b. inserting fluorocarbon emulsion into said space within said second container in an amount less than space space;
    c. sparging the space not occupied with said fluorocarbon emulsion with a second gas that is substantially inert to said fluorocarbon emulsion;
    d. inserting said first gas to be dissolved into said first container to expand said first container, withdrawing the substantially inert second gas from said space through the port of said second container, and allowing the first gas to permeate said first container;
    d. withdrawing oxygenated fluorocarbon emulsion from said second container through its port.

8. A method of dissolving a gas in a fluorocarbon emulsion, comprising;
    a. providing a first container and a second container, said first container having a fluorocarbon emulsion therein, wherein said second container is adapted to hold a gas, and wherein said first container is in contact with the interior of said second container through a wall that is permeable to said gas but not to said fluorocarbon emulsion; and
    b. inserting a gas in said second container and allowing the gas to permeate said first container to provide an oxygenated fluorocarbon emulsion in said first container.

9. The method of claim 8, wherein said first container is inside said second container.

10. The method of claim 8, wherein said second container is inside said first container.

11. The method of claim 8, wherein said gas is an oxygen containing gas.

* * * * *